US012665063B1

(12) United States Patent
Liu et al.

(10) Patent No.: US 12,665,063 B1
(45) Date of Patent: Jun. 23, 2026

(54) SYSTEMS AND METHODS FOR STANDARDIZING A PHARMACY PRESCRIPTION

(71) Applicant: Amazon Technologies, Inc., Seattle, WA (US)

(72) Inventors: Jianfeng Liu, Shoreline, WA (US); Cristobal Andres Pais, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

(21) Appl. No.: 18/541,714

(22) Filed: Dec. 15, 2023

(51) Int. Cl.
*G16H 20/10* (2018.01)
*G16H 10/60* (2018.01)

(52) U.S. Cl.
CPC ............. *G16H 20/10* (2018.01); *G16H 10/60* (2018.01)

(58) Field of Classification Search
CPC ............................... G16H 20/10; G16H 10/60
See application file for complete search history.

(56) References Cited

U.S. PATENT DOCUMENTS

| | | | | |
|---|---|---|---|---|
| 11,037,665 B2 * | 6/2021 | O'Keeffe | ............... | G16H 50/50 |
| 11,056,222 B1 * | 7/2021 | Nambirajan | ............. | G06N 5/01 |
| 2023/0290464 A1 * | 9/2023 | Diatto | .................... | G16H 20/10 |
| 2024/0221884 A1 * | 7/2024 | Lim | ....................... | G16H 80/00 |

FOREIGN PATENT DOCUMENTS

CN          115938608 A  *  4/2023

* cited by examiner

*Primary Examiner* — Sheetal R Paulson
(74) *Attorney, Agent, or Firm* — Knobbe, Martens, Olson & Bear, LLP

(57)          ABSTRACT

The present disclosure generally relates to systems and methods for inferring a standardized medication prescription from a medication prescription. A standardization engine of a prescription standardization system may receive a medication prescription and a request to standardize said medication prescription. In some cases, the standardization engine may normalize the medication prescription. In addition, the standardization engine, utilizing a machine learning model, may parse the medication prescription into atomic medical information. The machine learning model may infer a standardized medication prescription from the atomic medical information. In some embodiments, an active learning engine may be communicatively coupled to the standardization system. Systems and methods described herein also relate to the active learning engine to generate training sample sets (e.g., synthetic prescriptions) and train the machine learning model of the prescription standardization system.

14 Claims, 7 Drawing Sheets

100

| STANDARDIZATION ENGINE 104 | ACTIVE LEARNING ENGINE 106 |
| --- | --- |
| NORMALIZATION MODULE 108 | DATA AUGMENTATION MODULE 112 |
| INFERRING MODULE 110 | MANUAL INPUT MODULE 114 |

DOMAIN KNOWLEDGE DATA STORE 116

NETWORK 120

ML MODEL STORE 118

102

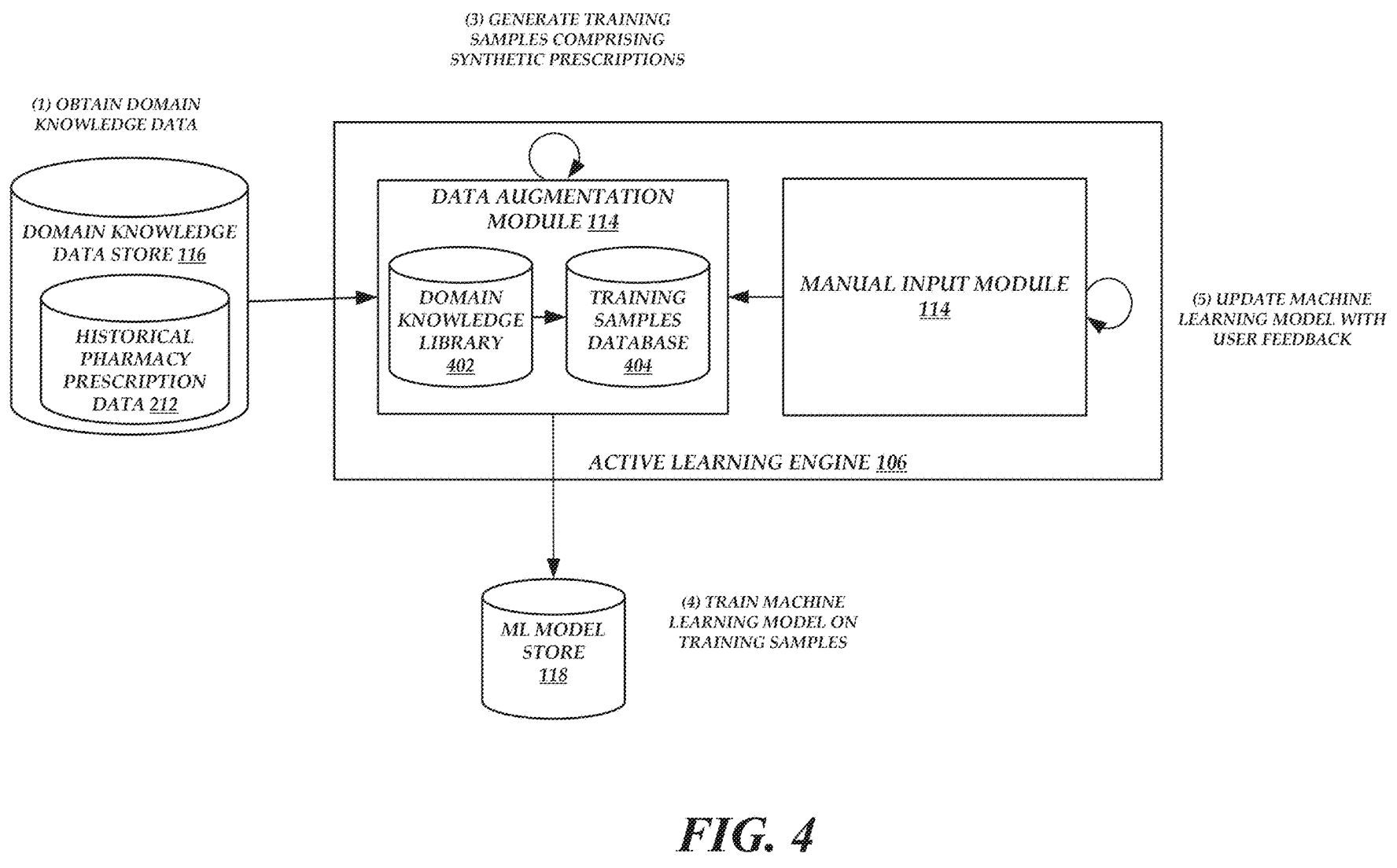

(5) UPDATE MACHINE
LEARNING MODEL WITH
USER FEEDBACK (3) GENERATE TRAINING
SAMPLES COMPRISING
SYNTHETIC PRESCRIPTIONS

MANUAL INPUT MODULE
114

ACTIVE LEARNING ENGINE 106

DATA AUGMENTATION
MODULE 114

DOMAIN
KNOWLEDGE
LIBRARY
402

TRAINING
SAMPLES
DATABASE
404

(4) TRAIN MACHINE
LEARNING MODEL ON
TRAINING SAMPLES

ML MODEL
STORE
118

(1) OBTAIN DOMAIN
KNOWLEDGE DATA

DOMAIN KNOWLEDGE
DATA STORE 116

HISTORICAL
PHARMACY
PRESCRIPTION
DATA 212

*FIG. 4*

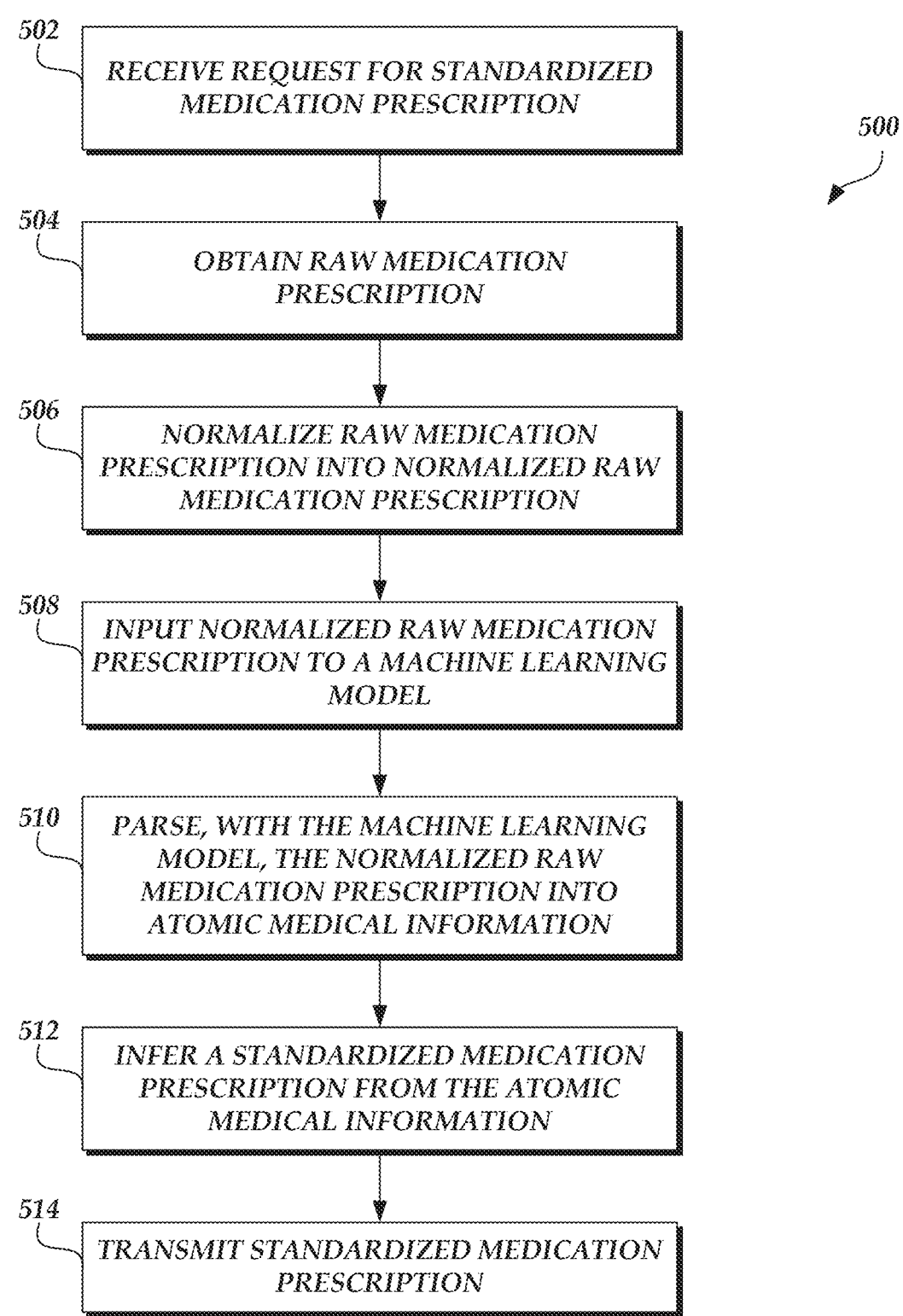

502 — RECEIVE REQUEST FOR STANDARDIZED MEDICATION PRESCRIPTION

500

504 — OBTAIN RAW MEDICATION PRESCRIPTION

506 — NORMALIZE RAW MEDICATION PRESCRIPTION INTO NORMALIZED RAW MEDICATION PRESCRIPTION

508 — INPUT NORMALIZED RAW MEDICATION PRESCRIPTION TO A MACHINE LEARNING MODEL

510 — PARSE, WITH THE MACHINE LEARNING MODEL, THE NORMALIZED RAW MEDICATION PRESCRIPTION INTO ATOMIC MEDICAL INFORMATION

512 — INFER A STANDARDIZED MEDICATION PRESCRIPTION FROM THE ATOMIC MEDICAL INFORMATION

514 — TRANSMIT STANDARDIZED MEDICATION PRESCRIPTION

602  OBTAIN DOMAIN KNOWLEDGE DATA

604  GENERATE LIBRARY TO STORE DOMAIN KNOWLEDGE DATA

606  GENERATE SET OF TRAINING SAMPLES BASED ON THE LIBRARY

608  TRAIN A ML MODEL ON THE SET OF TRAINING SAMPLES

610  UPDATE ML MODEL BASED ON USER FEEDBACK

SYSTEMS AND METHODS FOR STANDARDIZING A PHARMACY PRESCRIPTION

BACKGROUND

Medication prescriptions contain information about a medication (e.g., name, active ingredient), dosage, doctor notes, and other directions. Medication prescriptions are typically written by medical providers in the form of raw text and transmitted to pharmacies for processing and fulfillment. Medication prescriptions printed on labels should be accurate (e.g., in view of the prescription), safe (e.g., in view of patient context), consistent (e.g., to reduce confusion), and clear (e.g., avoid dosage confusion). However, medication prescriptions are typically generated using manual data entry and various intake processes that may introduce errors, delay, and inconsistencies. In addition, dosage calculations (e.g., hours of administration, maximum or minimum daily intake amount) and other necessary information may not be readily clear from a raw medication prescription transmitted from a medical provider.

BRIEF DESCRIPTION OF THE DRAWINGS

Various features will now be described with reference to the following drawings. Throughout the drawings, reference numbers may be re-used to indicate correspondence between referenced elements. The drawings are provided to illustrate examples described herein and are not intended to limit the scope of the disclosure.

FIG. 4 is a block diagram depicting the generation and utilization of training data by the active learning engine of the prescription standardization system;

FIG. 5 illustrates an example routine for inferring a standardized medication prescription from a medication prescription;

DETAILED DESCRIPTION

Figure 1:
FIG. 1 is a block diagram depicting an illustrative environment in which a prescription standardization system can provide standardized medication prescriptions.

Generally, aspects of the present disclosure relate to inferring standardized medication prescriptions from raw medication prescriptions. Raw medication prescriptions, including drug information, medical provider notes, and/or other medical information, may be sent directly to pharmacy systems for processing and fulfillment. Raw medication prescriptions may vary in detail, terminology, length, and even style. In addition, generation of pharmacy directions or labels from prescriptions by humans may be error prone (e.g., due to fatigue, accident, etc.), subjective due to human interpretations of data, and/or inconsistent. Pharmacists and other technicians fulfilling prescriptions typically infer additional information, such as dosage calculations, cadence, hours of administration, etc. that may not be readily apparent from the raw medication prescriptions. This inferred information may be passed along to patients to aid in administration. Processing and inferring by pharmacists may also serve as a final check on the prescription, to correct any mistakes or inconsistencies that may harm the patient.

In accordance with the present disclosure, the prescription standardization system may infer information from a raw medication prescription and generate a standardized medication prescriptions. The standardized medication prescription may include normalized language (e.g., standard drug names, standard abbreviations, chemical names, etc.) such that any pharmacist or technician can easily understand the prescribed directions. In addition, the standardized medication prescription may be apportioned into several easily understandable fields such that any pharmacist or patient can understand (e.g., minimal daily frequency, hours of administration, taken with food, etc.). To parse and infer the standardized medication prescription, the prescription standardization system may utilize a machine learning (ML) model. To parse and infer, the raw medication prescription may be input into the ML model, causing the ML model to parse the raw medication prescription, and output the standardized medication prescription.

Using a ML model to infer standardized medication prescriptions generally involves a large number of potential combinations of calculations and directions. For instance, thousands of prescriptions are processed by pharmacies every day, and (as an example) only tens of millions of examples may be available for training. To train an ML to predict a standardized medication prescription directly from a raw medication prescription may require billions of examples in a training dataset. However, even with a decades of historical prescriptions and medical provider notes available as training data, this may only be a fraction of the required billions of examples (e.g., $\frac{1}{100}$, $\frac{1}{1000}$, etc. of required data is available).

In some embodiments, the prescription standardization system may generate a standardized medication prescription based on atomic medical information parsed from a raw medication prescription. The atomic medical information parsed from the raw medication prescription may represent specific fields to be inferred in each standardized medication prescription (e.g., hours of administration, daily maximum, daily minimum, etc.). In this manner, the prescription standardization system may standardize raw medication prescriptions. This may, over time, generate additional training data that may be a higher quality (e.g., more certainty in inferred prescriptions) than existing training data.

The prescription standardization system may, in some embodiments, update the ML model. As described herein, the prescription standardization system may include an active learning engine to provide feedback to the ML model. As an example, the active learning engine may generate training data sets, such as based on historical prescriptions and medical provider notes, to continually train the ML model. In addition, pharmacists, medical providers, and other experts may provide feedback (e.g., corrections, new training sets, notes, etc.) directly to the prescription standardization system, such as via the active learning engine. The continual creation of training data sets may continue to train the ML model on current information.

As will be appreciated by one of skill in the art in light of the present disclosure, the embodiments disclosed herein improve the ability of computing systems, such as cloud-hosted computing systems, to determine standardized medication prescriptions. Moreover, the presently disclosed embodiments address technical problems inherent within computing systems; specifically, the difficulties in providing accurate predictions with limited training data and sufficient accuracy without oversized feature vectors. For instance, using a ML model to predict a standardized medication prescription from a raw, often sparse, medication prescription using domain knowledge may reduce feature vector size and increase computation performance. Moreover, using existing data sets, it is possible to train a plurality of ML models to predict discrete components, such as specific fields of medication prescription, (instead of the entire standardized medication prescription), with sufficient accuracy. These technical problems are addressed by the various technical solutions described herein, including a cloud-hosted computing system configured to provide predicted standardized medication prescriptions. Thus, the present disclosure represents an improvement on computing systems in general.

The foregoing aspects and many of the attendant advantages of this disclosure will become more readily appreciated as the same become better understood by reference to the following description, when taken in conjunction with the accompanying drawings.

FIG. 1 depicts an example prescription standardization system 100 in which embodiments of the present disclosure can be implemented by a standardization engine 104 to infer a standardized medication prescription from a medication prescription. The standardized medication prescription may be used by a pharmacy to fulfill prescriptions for a customer or patient, or may inform the customer or patient of the prescription including additional inferred information. For example, the standardized medication prescription may contain inferred information from the raw medication prescription, such as a minimal quantity per dose, a maximum quantity per dose, a daily administration minimum frequency, a daily administration maximum frequency, a cadence, hours of administration, or an average daily administration frequency.

As shown in FIG. 1, the prescription standardization system 100 may include user device(s) 102, a standardization engine 104, an active learning engine 106, a domain knowledge data store 116, and a ML model store 118. The components of the prescription standardization system 100 may be communicatively coupled via a network 120.

User device(s) 102 (hereinafter referred to as "user device 102" for ease of reference) illustratively correspond to any computing device that provides a means for a user to interact with components of prescription standardization system 100 such as standardization engine 104, the active learning engine 106, the domain knowledge data store 116, and the ML model store 118. User device 102 may include user interfaces or dashboards that connect a user with a machine, system, or device. In various implementations, user device 102 includes computer devices with a display and a mechanism for user input (e.g., mouse, keyboard, voice recognition, touch screen, and/or the like). For example, the user device 102 includes a desktop, tablet, e-reader, server, wearable device, laptop or tablet computer, smartphones, gaming consoles, personal digital assistants (PDAs), hybrid PDA/mobile phone, mobile phone, electronic book reader, set-top box, voice command device, camera, digital media player, and the like. The user device 102 can access a cloud provider network via the network 120 to view or manage their data and computing resources, as well as to use websites and/or applications hosted by the cloud provider network. Elements of the cloud provider network may also act as clients to other elements of that network. Thus, user device 102 can generally refer to any device accessing a network-accessible service as a client of that service.

In some embodiments, the user device 102 is a user device associated with a pharmacist or technician (referred to as "users") associated with a pharmacy to receive, standardize, and track prescriptions. In the case of technicians, the user device 102 may be a part of a data entry/intake process to service prescriptions for customers or patients. For instance, thousands of prescriptions per day may be processed by the prescription standardization system 100. In some systems, technicians of the prescription standardization system 100 may review the prescriptions (and any associated data) and generate pharmacy directions, so that pharmacists may fulfill orders for medication. In the case of pharmacists, the user device 102 may be a part of a prescription fulfillment process and the pharmacists may generate a standardized prescription and/or medication prescription.

The network 120 can include any appropriate network, including wired network, wireless network, or combination thereof. For example, network 120 may be a personal area network, local area network, wide area network, cable network, satellite network, cellular network, or any other such network or combination thereof. As a further example, the network 120 may be a publicly accessible network of linked networks, possibly operated by various distinct parties, such as the Internet. Protocols and components for communicating via the Internet or any other types of communication networks are known to those skilled in the art of computer communications and thus, need not be described in more detail herein. In various embodiments, the network 120 may be a private or semi-private network, such as a corporate or university intranet. The network 120 may include one or more wireless networks, such as a Global System for Mobile Communications (GSM) network, a Code Division Multiple Access (CDMA) network, a Long-Term Evolution (LTE) network, C-band, mmWave, sub-6 GHZ, or any other type of wireless network. The network 120 can use protocols and components for communicating via the Internet or any of the other aforementioned types of networks. For example, the protocols used by the network 120 may include Hypertext Transfer Protocol (HTTP), HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art of computer communications and thus, need not be described in more detail herein.

In various implementations, the network 120 can represent a network that may be local to a particular organization, e.g., a private or semi-private network, such as a corporate or university intranet. In some implementations, devices communicate via the network 120 without traversing an external network, such as the Internet. Devices connected via the network 120 in this case may be walled off from accessing the Internet. As an example, the network 120 may not be connected to the Internet. Accordingly, e.g., the user device 102 may communicate with the standardization engine 104 and/or active learning engine 106 directly (via wired or wireless communications) or via the network 120, without using the Internet. Thus, even if the network 120 or the Internet is down, active learning engine 106 may continue to communicate and function via direct communications (and/or via the network 120).

The standardization engine 104 may generate standardized medication prescriptions to label and/or accompany fulfilled prescriptions from medication prescriptions (e.g., prescriptions from medical providers). In some embodiments, the standardization engine 104 may receive a raw medication prescription (e.g., a written prescription) and generate a standardized medication prescription. As shown in FIG. 1, the standardization engine 104 includes normalization module 108 and inferring module 110.

Normalization module 108 may normalize the medication prescription. Medication prescriptions may be "raw" and may comprise text written by a medical provider or prescriber. In some examples, the medication prescription may contain errors, acronyms, incomplete information, alternative drug names, common pharmacological jargon, inconsistencies, and the like. In some embodiments, the normalization module 108 may normalize or standardize the terminology of a raw medication prescription. For example, a raw medication prescription may comprise a prescription for X milligrams of a certain medication in the form of "tablets." However, according to general pharmacy domain knowledge, X milligrams of the medication may only be manufactured in capsule form, rather than tablets. In this example, the normalization module 108 may verify the raw medication prescription using information stored in the domain knowledge data store 116. In addition, the normalization module 108 may normalize terms of the raw medication prescription according to the information stored in the domain knowledge data store 116. The normalization module 108 may identify, highlight, or flag errors in the raw medication prescription. Notifications, alerts, and/or messages may be generated by the normalization module 108 and transmitted to the appropriate user devices 102 for display, so as to notify a user of errors or a faulty prescription. An error alert generated by the normalization module 108 may be sent to the user device 102 of the prescriber, medical provider, pharmacist, etc.

In addition to the normalization module 108, the standardization engine 104 includes the inferring module 110. The inferring module 110 may infer a standardized medication prescription from the medication prescription. Alternatively, or in addition, the inferring module 110 may infer a standardized medication prescription from a normalized medication prescription from the normalization module 108.

Figure 7:
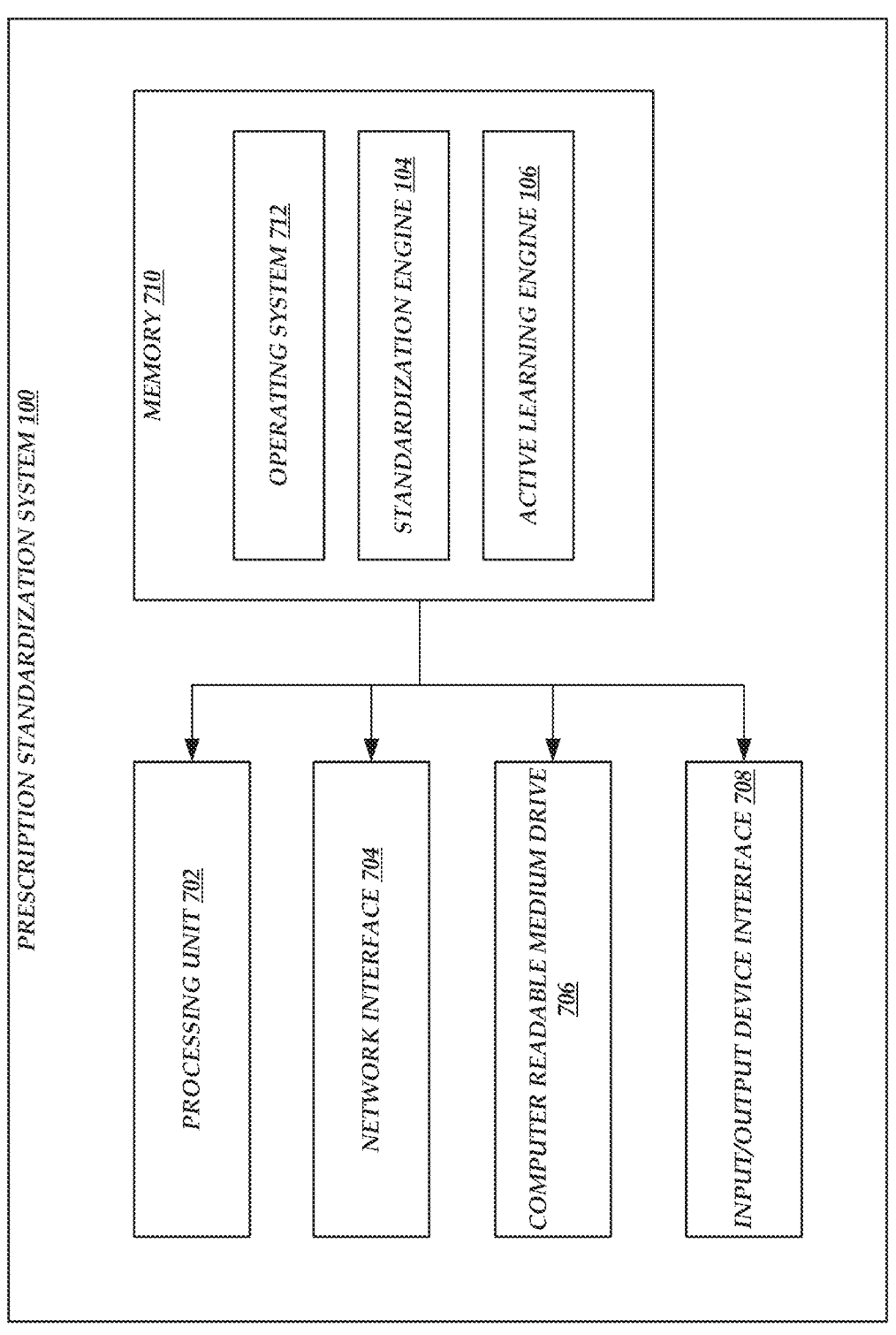
FIG. 7 is a block diagram illustrating components of an example computing system that can be used to implement the various systems and methods described herein.

The standardization engine 104 can be implemented on one or more server computing systems (such as depicted in FIG. 7), or alternatively, on a cloud provider network that can be accessed by user device 102 over a network 120. A cloud provider network (sometimes referred to simply as a "cloud"), refers to a pool of network-accessible computing resources (such as compute, storage, and networking resources, applications, and services), which may be virtualized or bare-metal. The cloud can provide convenient, on-demand network access to a shared pool of configurable computing resources that can be programmatically provisioned and released in response to customer commands. These resources can be dynamically provisioned and reconfigured to adjust to variable load. Cloud computing can thus be considered as both the applications delivered as services over a publicly accessible network (e.g., the Internet, a cellular communication network) and the hardware and software in cloud provider data centers that provide those services.

The cloud provider network may implement various computing resources or services, which may include a virtual compute service, data processing service(s) (e.g., map reduce, data flow, and/or other large scale data processing techniques), data storage services (e.g., object storage services, block-based storage services, or data warehouse storage services) and/or any other type of network based services (which may include various other types of storage, processing, analysis, communication, event handling, visualization, and security services). The resources required to support the operations of such services (e.g., compute and storage resources) may be provisioned in an account associated with the cloud provider, in contrast to resources requested by users of the cloud provider network, which may be provisioned in user accounts. The cloud provider network can include sets of host computing devices, where each set can represent a logical group of devices, such as a physical "rack" of devices. Each computing device can support one or more hosted machine instances that may be virtual machine instances, representing virtualized hardware supporting, e.g., an operating system and applications. Hosted machine instances may further represent "bare metal" instances, whereby a portion of the computing resources of the computing device directly support (without virtualization) the machine instance. In some cases, a machine instance may be created and maintained on behalf of a client. For example, a client may utilize a client computing device to request creation of a machine instance executing client-defined software. In other cases, machine instances may implement functionality of the cloud provider network itself. For example, machine instances may correspond to block storage servers, object storage servers, or compute servers that in term provide block storage, object storage, or compute, respectively, to client computing devices. While block storage, object storage, and compute are example services, machine instances can additionally or alternatively represent domain name services ("DNS") servers, relational database servers, servers providing serverless computing services, and other server services for supporting on-demand cloud computing platforms. Each host computing device includes hardware computer memory and/or processors, an operating system that provides executable program instructions for the general administration and operation of that server, and a computer-readable medium storing instructions that, when executed by a processor of the server, allow the server to perform its intended functions. Furthermore, the cloud provider network may include other computing devices facilitating operation of the host computing devices, such as data stores to store account information, computing devices to implement logging, monitoring, and billing services, etc.

In some implementations, the cloud provider network can provide on-demand, scalable computing platforms to users through the network 120, for example allowing users to have at their disposal scalable "virtual computing devices" via their use instances or services provided by such instances. These virtual computing devices have attributes of a personal computing device including hardware (various types of processors, local memory, random access memory ("RAM"), hard-disk and/or solid-state drive ("SSD") storage), a choice of operating systems, networking capabilities, and pre-loaded application software. Each virtual computing device may also virtualize its console input and output ("I/O") (e.g., keyboard, display, and mouse). This virtualization allows users to connect to their virtual computing device using a computer application such as a browser, application programming interface, software development kit, or the like, in order to configure and use their virtual computing device just as they would a personal computing device. Unlike personal computing devices, which possess a fixed quantity of hardware resources available to the user, the hardware associated with the virtual computing devices can be scaled up or down depending upon the resources the user requires. Users can choose to deploy their virtual computing systems to provide network-based services for their own use and/or for use by their customers or clients.

The active learning engine 106 may provide data augmentation to the components of the standardization engine 104, such as the normalization module 108 and the inferring module 110. For example, the active learning engine 106 may generate training data sets or samples to be used to train the ML model(s) stored in the ML model store 118. In addition, active learning engine 106 may be used to supplement, enrich, store, etc. domain knowledge data in the domain knowledge data store 116. As noted herein, the normalization module 108 may access the domain knowledge data store 116 in order to normalize the raw medication prescription. As shown in FIG. 1, the active learning engine 106 may include the data augmentation module 112 and the manual input module 114.

The data augmentation module 112 may generate training data for the ML model(s) stored in the ML model store 118. The data augmentation module 112 may generate training data based on domain knowledge data stored in the domain knowledge data store 116. The data augmentation module 112 may generate libraries to store pharmacist domain knowledge, e.g., specific logic used to infer mediation information. In addition, the data augmentation module 112 may generate training samples that mimic realistic prescriptions, e.g., synthetic (or simulated) prescriptions. The synthetic prescriptions may be used to train the ML model to infer standardized medication prescription from complex and various variations of real scenarios.

The manual input module 114 may receive feedback or input from users or experts in the field, such as pharmacists, doctors, technicians, medical providers, and other professionals. For example, the manual input module 114 may receive input relating to dataset labels, domain knowledge data, edits to synthetic prescriptions, and the like. The manual input module 114 may automatically or continuously collect and receive feedback from users. In some embodiments, the user feedback or input received by the manual input module 114 may be used to augment (e.g., update, improve, enrich, or enhance) the components of the prescription standardization system 100. Augmenting components of the prescription standardization system 100 may include expanding the domain knowledge data store 116 with additional information from users. This in turn may allow components of the prescription standardization system 100, such as the normalization module 108 and/or the inferring module 110, to generate the standardized medication prescription with improved accuracy.

In some implementations, the active learning engine 106 can be implemented on one or more server computing systems (such as depicted in FIG. 7), or alternatively, on a cloud provider network (e.g., that can be accessed by user device 102 over a network 120). A cloud provider network (sometimes referred to simply as a "cloud"), refers to a pool of network-accessible computing resources (such as compute, storage, and networking resources, applications, and services), which may be virtualized or bare-metal. The cloud can provide convenient, on-demand network access to a shared pool of configurable computing resources that can be programmatically provisioned and released in response to customer commands. These resources can be dynamically provisioned and reconfigured to adjust to variable load. Cloud computing can thus be considered as both the applications delivered as services over a publicly accessible network (e.g., the Internet, a cellular communication network) and the hardware and software in cloud provider data centers that provide those services.

Domain knowledge data store 116 may hold information relating to domain knowledge. Domain knowledge may refer to information, facts, or data relating to a specific industry or discipline. As used herein, domain knowledge data store 116 may hold domain knowledge data relating to medicine, pharmacy, and related fields. For example, domain knowledge data may include historical pharmacy direction data (e.g., past prescriptions), drug information, drug interaction information, drug dosage information, active ingredients information, inactive ingredients information, drug names (e.g., generic name, brand name), and the like. In some embodiments, domain knowledge data store 116 may be accessed and updated by pharmacists, doctors, medical providers, and other field experts in order to contain current and up-to-date information. In addition, domain knowledge data may include trade-specific information, such as abbreviations or short-hand phrases used by professionals, experts, or technicians in the field. For example, a raw medication prescription may contain the abbreviation "qAM" indicating that a prescribed medication is to be taken "once a day in the morning." Shorthand information and other trade-specific knowledge may be stored within the domain knowledge data store 116.

In some embodiments, the standardization engine 104 accesses one or more machine learning models to parse and infer a standardized medication prescription. The ML model store 118 may store more than one machine learning models to be accessed by various components of the prescription standardization system 100. The standardization engine 104 may access a single ML model stored in the ML model store 118 to infer a standardized medication prescription.

Figure 2:
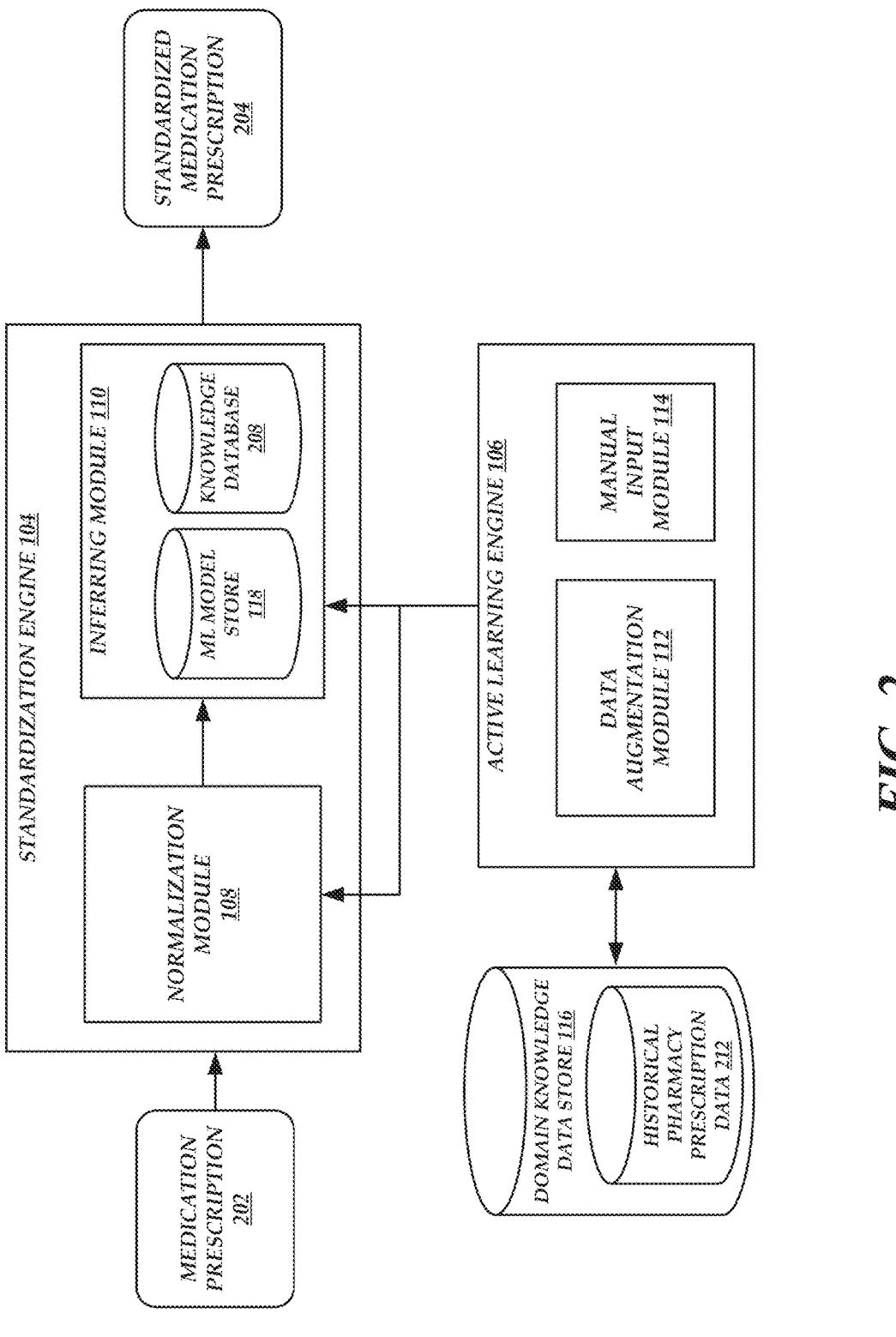
FIG. 2 is a block diagram depicting a prescription standardization system, in which a standardization engine and an active learning engine can provide standardized medication prescriptions.

FIG. 2 is a block diagram depicting a prescription standardization system 100, in which a standardization engine 104 and an active learning engine 106 can provide standardized medication prescriptions. The components of the prescription standardization system 100 may be implemented by a processor of a user device 102.

The prescription standardization system 100 may receive a medication prescription 202. For example, the prescription standardization system 100 may receive the medication prescription 202 from a user device, such as user device 102, or any other device. In some embodiments, the prescription standardization system 100 may receive the medication prescription 202 from a remote device, server, or other source, transmitted over the network 120.

The prescription standardization system 100 may receive the medication prescription 202 from another process or system. A pharmacy direction system, for example, may be associated with a pharmacy, a health insurance company, a medical provider, or any other appropriately licensed entity. The pharmacy direction system may determine a "predicted pharmacy direction" that is normalized to include consistent sentence structures, consistent terminology, etc. The predicted pharmacy direction generated by the pharmacy direction system may be transmitted to the prescription standardization system 100. As such, the prescription standardization system 100 may be coupled to the pharmacy direction system, or similar prediction-based prescription system, and receive predicted pharmacy directions to generate standardized medication prescriptions. An example of such a pharmacy direction system is disclosed in U.S. application Ser. No. 17/706,516, titled SYSTEMS AND METHODS FOR PREDICTING A PHARMACY DIRECTION, which is incorporated herein by reference in its entirety. The system disclosed therein predicts pharmacy directions using trained machine learning (ML) models and a pharmacy direction engine. The pharmacy direction engine may generate a pharmacy direction based on the predicted components of the pharmacy direction. For instance, the pharmacy direction engine may construct consistent sentence structures in accordance with a rule set.

The medication prescription 202 may include a prescription (e.g., written, typed) that may identify patient data (e.g., name, address), prescriber information, drug or controlled substance name, dosage form, drug strength, quantity, directions for use, intake frequency, refill options, date, and the like. In some embodiments, the medication prescription 202 is "raw" and may comprise text written by the prescriber or medical provider. For example, the raw medication prescription 202, in addition to patient data, may contain a line of text that reads "Amoxicillin 250 mg tablets, three times a day for seven days." In another example, the same prescription may be written by the prescriber utilizing abbreviations, and may be in the form of "Amoxicillin 250 mg tablets, TT tablets p.o. T.i.d.×7 days." The prescription standardization system 100 may receive any form of medication prescription, such as the form shown above, or similar. The medication prescription 202 may contain information in addition to the prescription, such as prescription notes, patient history information, prescriber information, and the like. For example, patient history information may indicate a quantity and frequency of a particular drug previously prescribed. Prescription notes may include any insurance information, alternative or substitute drugs, and/or any miscellaneous information related to the prescription.

As described herein, the standardization engine 104 may generate a standardized medication prescription 204 from the medication prescription 202. For example, the standardization engine 104 may parse a medication prescription 202 and infer a standardized medication prescription 204. In addition, the standardization engine 104 may utilize a ML model to infer the standardized medication prescription 204. The standardization engine 104 may output a standardized medication prescription 204 from the medication prescription 202 to label and/or accompany fulfilled prescriptions.

The normalization module 108 of the standardization engine 104 may normalize the medication prescription 202. Because the medication prescription 202 may contain text-based (e.g., written) directions from the prescriber, the medication prescription 202 may contain errors, acronyms, incomplete information, alternative drug names, common pharmacological jargon, inconsistencies, and the like. In normalizing the medication prescription 202, the normalization module 108 may fact-check the medication prescription 202 against the domain knowledge data store 116. Normalization may also correct past prescription processing errors and provide clear instructions to the patient. This may prevent prescription abuse and potential safety hazards to the patient.

The normalization module 108 normalizes or standardize the terminology of the medication prescription 202. To normalize the terminology of the medication prescription 202, the normalization module 108 may access the domain knowledge data store 116 to recognize terms within the medication prescription 202, such as drug names, abbreviations, common pharmacist terms. By using the domain knowledge data store 116 as a reference, the normalization module 108 may determine whether the medication prescription 202 contains outdated or inconsistent language. If outdated or inconsistent language is determined, the normalization module 108 may replace certain terms in the medication prescription 202 with verified or standardized terms. For example, the medication prescription 202 may contain terminology inconsistent with current brand names of certain drugs. In an example, the medication prescription 202 may contain a heartburn prescription for "Losec," rather than the updated name "Prilosec." The medication prescription 202 may, utilizing the domain knowledge data store 116, update the medication prescription 202 by replacing "Losec" with "Prilosec."

In some embodiments, the normalization module 108 may authenticate the medication prescription 202. Authenticating the medication prescription 202 includes verifying the medication prescription 202 against the domain knowledge data store 116 to correct or flag potential mistakes in the medication prescription 202. This may include misspellings of drug names, incorrect drug dosage prescriptions, incorrect or inconsistent administration direction, and the like. To authenticate, the normalization module 108 may identify certain drug names, abbreviations, common terms by referencing the domain knowledge data store 116. If the normalization module 108 identifies a drug name that appears similar to a correct drug name as listed in the domain knowledge data store 116, the normalization module 108 may flag the drug name for review, such as manual review by a pharmacist, etc. In another example, the normalization module 108 may determine an anomaly in the quantity of a drug prescribed (e.g., a quantity far exceeding historical prescriptions stored in the domain knowledge data store 116.

The normalization module 108 may identify an anomaly in the quantity of a drug prescribed (e.g., a quantity far exceeding historical prescriptions), an inconsistency in the directions for use (e.g., prescribing a topical medication to be ingested), or an incorrect drug name. Each error or anomaly identified by the normalization module 108 may be determined according to information in the domain knowledge data store 116. To flag an inconsistency in the directions for use, the normalization module 108 may first identify the type of medication. In addition, the normalization module 108 may identify that the prescribed medication does not match directions for use. In a non-limiting example, the normalization module 108 may identify, within the medication prescription 202, a prescription for "spironolactone cream," typically prescribed to treat hormonal acne. However, the medication prescription 202 in this example may also contain language directing the patient to "ingest a tablet once daily." The normalization module 108 may identify a potential error in the medication prescription 202 by looking up "spironolactone" in the domain knowledge data store 116 and identifying administration methods. Because ingestion of a "tablet" is likely to not be found under administration methods of "spirolactone cream," the normalization module 108 will flag the drug as a potential error. In addition, the normalization module 108 may identify an error in a prescriber's dosage calculation. For example, the normalization module 108 may identify an error when a prescriber directs the patient in the medication prescription 202 to "take 1 tablet daily for a week, the weekly dosage to not exceed 4 tablets."

Notifications, alerts, and/or messages may be generated by the normalization module 108 and transmitted to the appropriate user devices 102 for display. For example, the notifications may identify an anomaly warning, a request for additional information, an error in dosage calculation, a faulty prescription, and the like. In some embodiments, an error alert generated by the normalization module 108 is sent to the user device 102 of the prescriber, medical provider, pharmacist, technician, etc.

As such, the normalization module 108 may generate, from the medication prescription 202, a normalized medication prescription. In some embodiments, the normalized medication prescription may be used by the standardization engine 104 for further processing in generating the standardized medication prescription 204.

Once the medication prescription has been normalized, the inferring module 110 may infer information pertaining to a medication prescription 202 that a pharmacist would typically make in order to standardize the medication prescription. For example, dosage calculations may not be readily readable from a raw medication prescription 202, and would typically need to be calculated by the pharmacist fulfilling the prescription.

Thus, the inferring module 110 may infer a dosage calculation. In inferring, the inferring module 110 may generate the standardized medication prescription 204, which may include any information pertaining to the medication prescription 202 that a pharmacist would provide or supplement. In this regard, the standardized medication prescription 204 may comprise a number of fields, each relating to an aspect of the medication prescription 202. Each field may be related to information needed by a pharmacist, technician, or patient to understand the prescription. For example, fields may include a minimal quantity per dose, a maximum quantity per dose, a daily administration minimum frequency, a daily administration maximum frequency, a cadence, hours of administration, or an average daily administration frequency. As such, the inferring module 110 may infer each field from the atomic medical information of a medication prescription 202 and include the fields in the standardized medication prescription as appropriate.

As shown in FIG. 2, to conduct such inferring, the inferring module 110 may access the ML model stored in the ML model store 118. Although the ML model store 118 is shown as a component within the inferring module 110, the ML model store 118 may be located remotely and accessible by the inferring module 110 via the network 120. The ML model may be a large language model (LLM) or any similar AI model, neural network, etc. that has been trained on vast amount of text and can understand and analyze text-based content. In addition, the ML model may be a multi-task LLM that can output a plurality of inferred piece of information (e.g., in the form of a standardized medication prescription) at once. The inferring module 110 may access more than one ML model stored in the ML model store 118 to conduct such inferring. Alternatively, the inferring module 110 may access a single multi-task LLM to conduct such inferring and output a standardized medication prescription.

Once the ML model is accessed, the inferring module 110 may input the normalized medication prescription into the ML model. In response to the input, the ML model may parse the normalized medication prescription and infer the standardized medication prescription from the parsed medication prescription ("atomic medical information"). The inferring module 110 may input all or a portion of the medication prescription into the ML model. For example, the inferring module 110 may input only the directions portion (as opposed to the drug information) of a medication prescription into the ML model to be parsed into atomic medical information. As used herein, "atomic" medical information may include the normalized medication prescription apportioned, broken down, or separated, into individual or sectioned portions. Parsing the normalized medication prescription may be integrated as an initial task to be executed by the ML model in inferring the standardized medication prescription 204. To parse the normalized medication prescription, the ML model may access the domain knowledge data store 116 to recognize terms within the normalized medication prescription, such as drug names, abbreviations, common pharmacist terms. By using the domain knowledge data store 116 as a reference, the ML model may identify each term of the normalized medication prescription.

In addition, once the medication prescription 202 is parsed, the ML model may output a standardized medication prescription 204. The standardized medication prescription 204 includes any information considered relevant to a patient, pharmacist, technician, in the context of a prescription. In addition, the standardized medication prescription 204 includes any information that would have been inferred and included by a pharmacist. For example, the ML model may, in response to the atomic medical information, output the standardized medication prescription 204 corresponding to a minimal quantity per dose, a maximum quantity per dose, a daily administration minimum frequency, a daily administration maximum frequency, a cadence, hours of administration, or an average daily administration frequency. The standardized medication prescription 204 may include more or less output information relating to the medication prescription 202. In an example, a medication prescription 202 may include the following text: "take up to 3 tablets of X at 8:00 AM and 6:00 PM on weekdays." After normalization and parsing, the ML model may output the standardized medication prescription 204, consisting of the following fields: minimal quantity per dose=1; maximal quantity per dose=3, daily administration minimal frequency=twice daily; daily administration maximal frequency=twice daily; cadence=five days weekly on weekdays; hours of administration=8:00 a.m. and 6:00 p.m.; average daily administration frequency=10/7.

In some embodiments, the inferring module 110 may calculate a dosage calculation based on the atomic medical information. For example, the inferring module 110 may calculate an average daily administration frequency based on information provided in the medication prescription 202. In this case, the medication prescription 202 may contain the following text directed to administration of a prescribed medication: "three times daily (every 8 hours), three days weekly on Monday, Wednesday, and Friday." The inferring module 110 may infer, from this medication prescription 202, that the average daily administration frequency is 9/7, to account for the three times daily over three days weekly.

In some embodiments, the inferring module 110 may access a knowledge database 208. The knowledge database 208 may be stored locally within the inferring module 110, stored remotely and accessible via the network 120. The knowledge database 208 may store information from the domain knowledge data store 116, such as a subset of the information stored in the domain knowledge data store 116. Alternatively, the knowledge database 208 may be the domain knowledge data store 116, accessible via network 120. The inferring module 110 may augment, enrich, supplement, or revise the output of the ML model with information from the knowledge database 208. For example, the medication prescription 202 may include the direction "take 1 tablet by mouth every day in the morning." Although the standardization engine 104 may normalize and parse the medication prescription 202, the medication prescription 202 does not specify an hour of administration (HOA). For example, "in the morning" may refer to different hours in the morning (e.g., 8 a.m., 10 a.m.). In this example, the inferring module 110 may supplement the standardized medication prescription 204 with the medication's standard administration and/or patient history.

The standardized medication prescription 204 may be output by the standardization engine 104. As noted herein, the standardized medication prescription 204 may contain various fields corresponding to the inferred information from the 202, such as a minimal quantity per dose, a maximum quantity per dose, a daily administration minimum frequency, a daily administration maximum frequency, a cadence, hours of administration, or an average daily administration frequency. In some embodiments, the standardized medication prescription 204 is transmitted to the user device 102.

As shown in FIG. 2, the standardization engine 104 may be communicatively coupled to the active learning engine 106. The active learning engine 106 may augment (e.g., train, supplement, enrich, etc.) information utilized by the components of the standardization engine 104. Augmenting information utilized by components of the standardization engine 104 may include expanding the domain knowledge data store 116 to include additional information from users. This in turn may allow components of the prescription standardization system 100, such as the normalization module 108 and/or the inferring module 110, to generate standardized medication prescription with improved accuracy. In addition, the active learning engine 106 may generate training data sets to train the ML model(s) stored in the ML model store 118. To generate training data sets, the active learning engine 106 may access the domain knowledge data store 116, such as via network 120. The domain knowledge data stored in the domain knowledge data store 116 may inform the active learning engine 106 with relevant information, such as historical pharmacy data, etc. to be integrated into training data sets.

Domain knowledge data store 116 may hold domain knowledge data relating to medicine, pharmacy, and related fields. For example, domain knowledge data may include historical pharmacy direction data (e.g., past prescriptions), drug information, drug interaction information, drug dosage information, active ingredients information, inactive ingredients information, drug names (e.g., generic name, brand name), and the like. In some embodiments, the domain knowledge data store 116 includes historical pharmacy prescription data 212. Historical pharmacy prescription data 212 may include any information related to past prescriptions, directions, notes by medical providers or pharmacists, and the like.

The active learning engine 106 may generate new training data sets to train ML model(s). The generation of new training data sets in the form of synthetic prescriptions allows the ML model(s) to be trained to infer crucial and/or standardized information from medication prescriptions. For example, the data augmentation module 112 may generate new training data sets based on the domain knowledge data. To generate training data sets, the data augmentation module 112 may obtain the domain knowledge data from the domain knowledge data store 116, such as via the network 120.

In addition, the data augmentation module 112 may generate a library or series of libraries to store the obtained domain knowledge data. To generate the libraries, the data augmentation module 112 may access the domain knowledge data store 116 to obtain the domain knowledge data. Once accessed, the data augmentation module 112 may generate libraries to organize the retrieved domain knowledge data. The libraries generated by the data augmentation module 112 may be stored in a local data store in the data augmentation module 112 and/or the active learning engine 106. Alternatively, the data augmentation module 112 may generate and fill libraries to be stored in a remote location, and accessible via the network 120. Each library may comprise any data management or organization system maintained by the data augmentation module 112 to organize the domain knowledge data. For example, the data augmentation module 112 may generate a library with subfolders and/or subsections to organize domain knowledge data specific to historic prescriptions of a certain drug (e.g., organized by date, patient, dosage level). In this example, the data augmentation module 112 may create a library to hold all information related to a particular drug, with subsections relating to prescriptions including said drug, prescriber notes relating to said drug, pharmacist notes relating to said drug, etc. In another example, the data augmentation module 112 may generate a library or subfolder containing common prescription language and/or prescription abbreviations (e.g., "a.c."=before meals, "q.h.s"=every night at bedtime, "p.r.n"=as needed). The libraries may be stored locally within the active learning engine 106, or may be stored remotely and accessible via a server or network. The data augmentation module 112 may update the library, e.g., on a periodic basis.

The data augmentation module 112 may generate training samples based on the contents of the libraries. Training samples may include synthetic or simulated prescriptions that mimic realistic prescriptions. In some embodiments, the data augmentation module 112 may utilize the contents of the libraries, such as domain knowledge corresponding to a particular drug and/or historic prescription data, to generate synthetic prescriptions. In addition, the data augmentation module 112 may utilize any rule-based or generative artificial intelligence (AI) approach to generate the training samples.

The data augmentation module 112 may generate a synthetic prescription based on any variation of content from the libraries. To generate a synthetic prescription, the data augmentation module 112 may access a historical prescription from the historical pharmacy prescription data 212 of the domain knowledge data store 116. In response, the data augmentation module 112 may edit, omit, or add information to the historical prescription. Revisions, addition, or omissions to the historical prescriptions may model real-world scenarios, such as typos, missing information, unnecessary information, etc. Generating synthetic prescriptions from historical prescriptions may result in realistic prescriptions. This in turn may help train the ML model to handle a variety of scenarios. The level of difficulty of each synthetic prescription may be tailored by the data augmentation module 112. For example, the data augmentation module 112 may generate simple synthetic prescriptions intended to be an "easy" case (e.g., a prescription with all the inferred information explicitly included). The data augmentation module 112 may also generate complex prescriptions with missing information, incorrect or inconsistent information, and/or other difficult variations of real scenarios. For example, a synthetic prescription may contain a complex intake direction, such as "twice a day every day three days at 8 a.m. and 6 p.m., excluding weekends" or the like. In some examples, the data augmentation module 112 may generate a synthetic prescription based on a subset of information from the libraries.

Synthetic prescriptions and/or other training data may be tailored, such as to provide targeted training for the ML model(s). For example, synthetic prescriptions focused on training the ML model(s) to infer complex dosage calculations may be generated by the data augmentation module 112. In this example, the data augmentation module 112 may retrieve or access libraries pertaining to historic prescriptions containing complex dosage directions in order to generate similar synthetic prescriptions.

In generating the synthetic prescriptions, the data augmentation module 112 may label each synthetic prescription with the appropriate "correct" inferred information. For example, the data augmentation module 112 may generate a synthetic prescription that reads: "take 1 to 2 tablets by mouth daily." In this example, the data augmentation module 112 may label each portion of the synthetic prescription with the correct inferred output. The following labels may be applied to each portion of the synthetic prescription: minimal quantity per dose="1"; maximal quantity per dose="2"; daily administration minimal frequency="[once] daily"; daily administration maximal frequency="[once] daily"; cadence="daily"; hours of administration=N/A; average daily administration frequency="1." In some embodiments, more or less labels may be given to the synthetic prescription. The synthetic prescriptions and/or other training data sets may be stored in the libraries maintained by the data augmentation module 112 or elsewhere and accessible via servers or networks, such as network 120.

The active learning engine 106 may incorporate feedback and/or novel knowledge from users, such as medical providers, pharmacists, and the like. Feedback from users may be used to tune and/or improve aspects of the active learning engine 106, and ultimately aspects of the prescription standardization system 100. To incorporate feedback and/or novel knowledge, the manual input module 114 may receive user input. For example, the user input may relate to a correction in a synthetic prescription, a corrected label of a synthetic prescription, an intent of a specific note, etc.

The active learning engine 106 (and/or the data augmentation module 112) may conduct the training of the ML model(s) stored in the ML model store 118. For example, the ML model(s) may be trained on a specific set of synthetic prescriptions generated by the data augmentation module 112. In some embodiments, the active learning engine 106 and/or data augmentation module 112 may conduct training on the ML model(s) in order to train the ML model(s) to infer a specific set of information from a medication prescription. The active learning engine 106 and/or data augmentation module 112 may conduct training to train the ML model(s) to infer all requested information from a medication prescription. In addition to training the ML model(s), the active learning engine 106 may supplement or provide feedback to the normalization module 108.

Figure 3:
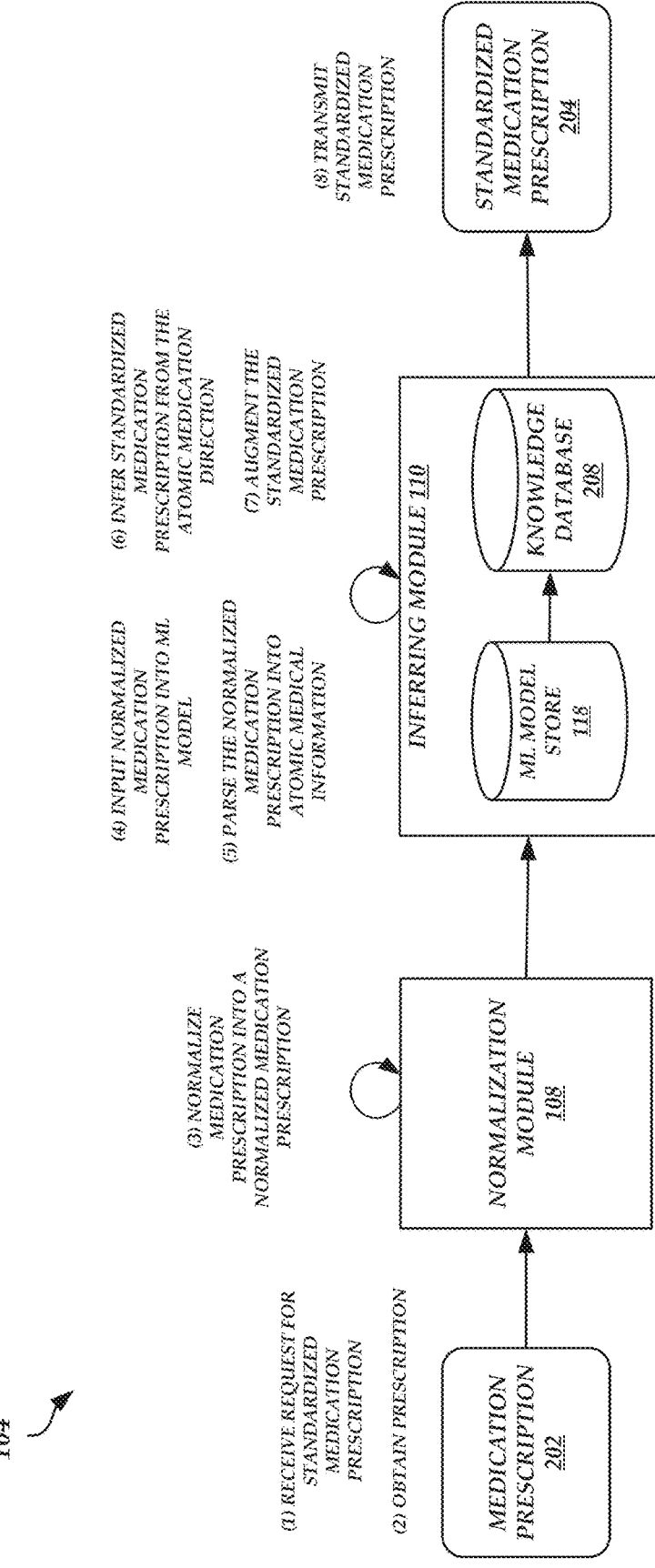
FIG. 3 is a block diagram depicting sample input to, and output from, a standardization engine implemented by the prescription standardization system.

FIG. 3 is a block diagram depicting sample input to, and output from, a standardization engine 104 implemented by the prescription standardization system 100. As noted herein, the prescription standardization system 100 may infer a standardized medication prescription 204 from a medication prescription 202.

At (1), the standardization engine 104 may receive a request for a standardized medication prescription. In some embodiments, the standardization engine 104 may receive a request for the standardized medication prescription from a user, such as a pharmacist, pharmacy technician, etc. of user device 102. Accordingly, at (2), the standardization engine 104 may obtain a medication prescription 202. The medication prescription may correspond to the request for the standardized medication prescription. For example, the request for the standardized medication prescription may include the medication prescription 202. Alternatively, or in addition, the medication prescription 202 corresponding to the request may be accessed and/or obtained by the standardization engine 104 from a different source, such as a server, database, etc. For example, the medication prescription 202 may transmitted from the prescriber network to the standardization engine 104. The prescription standardization system 100 may receive the medication prescription 202 from a remote device, server, or other source, transmitted over the network 120.

As noted herein, the medication prescription 202 may include a prescription (e.g., written, typed) that may identify patient data (e.g., name, address), prescriber information, drug or controlled substance name, dosage form, drug strength, quantity, directions for use, intake frequency, refill options, date, and the like. In some embodiments, the medication prescription 202 is "raw" and may comprise text written by the prescriber or medical provider. For example, the raw medication prescription 202, in addition to patient data, may contain a line of text that reads "Amoxicillin 250 mg tablets, three times a day for seven days." In another example, the same prescription may be written by the prescriber utilizing abbreviations, and may be in the form of "Amoxicillin 250 mg tablets, TT tablets p.o. T.i.d.×7 days." The prescription standardization system 100 may receive any form of medication prescription, such as the form shown above, or similar. The medication prescription 202 may contain information in addition to the prescription, such as prescription notes, patient history information, prescriber information, and the like. For example, patient history information may indicate a quantity and frequency of a particular drug previously prescribed. Prescription notes may include any insurance information, alternative or substitute drugs, and/or any miscellaneous information related to the prescription.

At (3), the standardization engine 104 may normalize the medication prescription 202 into a normalized medication prescription. In some embodiments, the standardization engine 104 may omit normalization of the medication prescription 202 if the medication prescription 202 has already been normalized by an external process or system.

To normalize the medication prescription 202, the normalization module 108 may standardize or normalize the terminology of the medication prescription 202. As noted herein, the medication prescription 202 may contain text-based directions from the prescriber. As such, the medication prescription 202 may contain errors, acronyms, incomplete information, alternative drug names, common pharmacological jargon, inconsistencies, and the like. In normalizing the medication prescription 202, the normalization module 108 may fact-check the medication prescription 202 against the domain knowledge data store 116. Normalization may also correct past prescription processing errors and provide clear instructions to the patient. This may prevent prescription abuse and potential safety hazards to the patient. In some embodiments, the normalization module 108 may access the domain knowledge data store 116 in order to determine or obtain standardized terminology. For example, the normalization module 108 may replace outdated terminology (e.g., drug names, abbreviations) with current terminology.

In addition, to normalizing the medication prescription 202, the normalization module 108 may verify or authenticate the medication prescription 202 according to domain knowledge. In some embodiments, authenticating the medication prescription 202 includes verifying the medication prescription 202 against the domain knowledge data store 116. For example, the normalization module 108 may identify, highlight, or flag errors in the medication prescription 202. The normalization module 108 may identify an anomaly in the quantity of a drug prescribed (e.g., a quantity far exceeding historical prescriptions), an inconsistency in the directions for use (e.g., prescribing a topical medication to be ingested), incorrect drug name. In addition, the normalization module 108 may identify an error in a prescriber's dosage calculation. For example, the normalization module 108 may identify an error when a prescriber directs the patient to "take 1 tablet daily for a week, the weekly dosage to not exceed 4 tablets."

In addition to normalizing the medication prescription 202, the normalization module 108 generates a notification or alert. For example, the notifications may identify an anomaly warning, a request for additional information, an error in dosage calculation, a faulty prescription, and the like. In some embodiments, an error alert generated by the normalization module 108 is sent to the prescriber, medical provider, pharmacist, technician, etc.

In addition, at (3), the normalization module 108 may generate, from the medication prescription 202, a normalized medication prescription. In some embodiments, the normalized medication prescription may be used by the standardization engine 104 for further processing in generating the standardized medication prescription 204. For example, the normalization module 108 may transmit the normalized medication prescription to the inferring module 110.

At (4), the inferring module 110 may input the normalized medication prescription into a ML model. The inferring module 110 may input the normalized medication prescription into a single ML model configured to infer the standardized medication prescription 204, which may include several pieces of inferred information from the medication prescription 202. Alternatively, or in addition, inferring module 110 may input the normalized medication prescription into multiple ML models configured to inter the standardized medication prescription 204.

In addition, at (5), the ML model may parse the normalized medication prescription into atomic medical information. For example, to parse the normalized medication prescription, the ML model may divide, separate, or apportion the medication prescription 202 into atomic medical information. For example, a sample medication prescription 202 may comprise a prescription that reads: "take 1 Levoxyl tablet orally every day." The ML model may divide the medication prescription 202 by separating the drug name "Levoxyl" from the drug type "tablet" from the directions for use "orally every day." In some embodiments, the inferring module 110 may utilize any AI-based or ML model, such as the ML model(s) stored in the ML model store 118 to parse the medication prescription 202. Alternatively, or in addition, the inferring module 110 may utilize any algorithm, process, or method other than machine learning to parse the medication prescription 202. In some examples, the inferring module 110 may output atomic medical information based on the medication prescription 202.

At (6), the inferring module 110 may infer, using a ML model, the standardized medication prescription 204. As shown in FIG. 3, the inferring module 110 may access the ML model stored in the ML model store 118. Although the ML model store 118 is shown as a component within the inferring module 110, the ML model store 118 may be located remotely and accessible by the inferring module 110 via the network 120. To infer the standardized medication prescription 204, the inferring module 110 may input the medication prescription 202 into the ML model. In response to the medication prescription 202 into the ML model, the ML model may output a standardized medication prescription 204. In some embodiments, the standardized medication prescription 204 comprises a number of fields, each relating to an aspect of the medication prescription 202. Each field may be related to information crucial for a pharmacist, technician, or patient to understand the prescription. For example, fields may include a minimal quantity per dose, a maximum quantity per dose, a daily administration minimum frequency, a daily administration maximum frequency, a cadence, hours of administration, or an average daily administration frequency. As such, the inferring module 110 may infer each field from the atomic medical information of a medication prescription 202.

At (7), the inferring module 110 may augment the standardized medication prescription 204. As shown in FIG. 3, the inferring module 110 may include and/or access the knowledge database 208. The knowledge database 208 may store information from the domain knowledge data store 116, such as a subset of the information stored in the domain knowledge data store 116. In addition, the inferring module 110 may augment (e.g., enrich, supplement, or revise) the output of the ML model with information from the knowledge database 208. For example, the medication prescription 202 may include the direction "take 1 tablet by mouth every day in the morning." Although the standardization engine 104 may normalize and parse the medication prescription 202, the medication prescription 202 may not specify an hour of administration (HOA). For example, "in the morning" may refer to different hours in the morning (e.g., 8 a.m., 10 a.m.). Accordingly, the inferring module 110 may supplement the standardized medication prescription 204 with the medication's standard administration and/or patient history.

At (8), the standardization engine 104 may transmit the standardized medication prescription 204. For example, the standardization engine 104 may transmit the standardized medication prescription 204 to the user device 102 and/or other device or system. In some embodiments, the standardization engine 104 transmits the standardized medication prescription 204 to a pharmacy to be accessed by a pharmacist or technician. In addition, the standardized medication prescription 204 may be transmitted to a pharmacy to be printed with the corresponding filled prescription. In some examples, the standardized medication prescription 204 is transmitted directly to a user or patient.

FIG. 4 is a block diagram depicting the generation and utilization of training data by the active learning engine 106 of the prescription standardization system 100. As described herein, the active learning engine 106 may train, supplement, enrich, and/or augment information utilized by the components of the standardization engine 104. In addition, the active learning engine 106 may generate training data sets to train the ML model(s) stored in the ML model store 118.

In some embodiments, the active learning engine 106 may access the domain knowledge data store 116, such as via network 120. Accordingly, at (1), the active learning engine 106 may obtain domain knowledge data stored in the domain knowledge data store 116. Domain knowledge data store 116 may hold domain knowledge data relating to medicine, pharmacy, and related fields. For example, domain knowledge data may include historical pharmacy direction data (e.g., past prescriptions), drug information, drug interaction information, drug dosage information, active ingredients information, inactive ingredients information, drug names (e.g., generic name, brand name), and the like. The domain knowledge data store 116 includes historical pharmacy prescription data 212. Historical pharmacy prescription data 212 may include any information related to past prescriptions, directions, notes by medical providers or pharmacists, and the like. In some embodiments, the data augmentation module 112 of the active learning engine 106 may obtain the domain knowledge data at (1).

The data augmentation module 112 of the active learning engine 106 may perform various processes to improve and augment the components of the prescription standardization system 100. Accordingly, at (2), the data augmentation module 112 of the active learning engine 106 may generate a library (or set of libraries) to store domain knowledge data from the domain knowledge data store 116. Each library may comprise any data management or organization system maintained by the data augmentation module 112 to organize the domain knowledge data. For example, the data augmentation module 112 may generate a library with subfolders and/or subsections to organize domain knowledge data specific to historic prescriptions of a certain drug (e.g., organized by date, patient, dosage level). In this example, the data augmentation module 112 may create a library to hold all information related to a particular drug, with subsections relating to prescriptions including said drug, prescriber notes relating to said drug, pharmacist notes relating to said drug, etc. In another example, the data augmentation module 112 may generate a library or subfolder containing common prescription language and/or prescription abbreviations (e.g., "a.c."=before meals, "q.h.s"=every night at bedtime, "p.r.n"=as needed). In some embodiments, the libraries may be stored locally within the active learning engine 106, or may be stored remotely and accessible via a server or network. In addition, the data augmentation module 112 may update the library, e.g., on a periodic basis.

At (3), the data augmentation module 112 may generate training samples and/or datasets based on the content of the library. In some embodiments, the training samples may comprise simulated or synthetic prescriptions that mimic realistic prescriptions. To generate the training samples, the data augmentation module 112 may utilize the contents of the libraries, such as domain knowledge corresponding to a particular drug and/or historic prescription data, to generate synthetic prescriptions. In addition, the data augmentation module 112 may utilize any rule-based or generative artificial intelligence (AI) approach to generate the training samples.

In some embodiments, the data augmentation module 112 generates a synthetic prescription based on any variation of content from the libraries. For example, the data augmentation module 112 may generate simple synthetic prescriptions intended to be an "easy" case (e.g., a prescription with all the inferred information explicitly included). The data augmentation module 112 may also generate complex prescriptions with missing information, incorrect or inconsistent information, and/or other difficult variations of real scenarios. For example, a synthetic prescription may contain a complex intake direction, such as "twice a day every day three days at 8 a.m. and 6 p.m., excluding weekends" or the like. In some examples, the data augmentation module 112 may generate a synthetic prescription based on a subset of information from the libraries.

Synthetic prescriptions and/or other training data may be tailored, such as to provide targeted training for the ML model(s). For example, synthetic prescriptions focused on training the ML model(s) to infer complex dosage calculations may be generated by the data augmentation module 112. In this example, the data augmentation module 112 may retrieve or access libraries pertaining to historic prescriptions containing complex dosage directions in order to generate similar synthetic prescriptions.

In generating the synthetic prescriptions, the data augmentation module 112 may label each synthetic prescription with the appropriate "correct" inferred information. For example, the data augmentation module 112 may generate a synthetic prescription that reads: "take 1 to 2 tablets by mouth daily." In this example, the data augmentation module 112 may label each portion of the synthetic prescription with the correct inferred output. Here, the following labels may be applied to each portion of the synthetic prescription: minimal quantity per dose="1"; maximal quantity per dose="2"; daily administration minimal frequency="[once] daily"; daily administration maximal frequency="[once] daily"; cadence="daily"; hours of administration=N/A; average daily administration frequency="1." In some embodiments, more or less labels are given to the synthetic prescription.

In addition, at (3), the data augmentation module 112 may store the training samples in a training samples database 404. The training samples database 404 may be stored or located within the data augmentation module 112. In some embodiments, the training samples database 404 may be located remotely and accessible via a server or network, such as the network 120.

At (4), the ML model(s) stored in the ML model store 118 may be trained on the generated training samples. The active learning engine 106 (and/or the data augmentation module 112) may conduct the training of the ML model(s) stored in the ML model store 118. For example, the ML model(s) may be trained on a specific set of synthetic prescriptions generated by the data augmentation module 112. The active learning engine 106 and/or data augmentation module 112 may conduct training on the ML model(s) in order to train the ML model(s) to infer a specific set of information from a medication prescription. In some embodiments, the active learning engine 106 and/or data augmentation module 112 may conduct training to train the ML model(s) to infer all requested information from a medication prescription.

At (5), the ML model(s) may be updated or improved. For example, the manual input module 114 may receive user input related to any aspect of the prescription standardization system 100. For example, feedback from users may be used to tune and/or improve aspects of the ML model(s), active learning engine 106, and ultimately aspects of the prescription standardization system 100. To incorporate feedback and/or novel knowledge, the manual input module 114 may receive user input. For example, the user input may relate to a correction in a synthetic prescription, a corrected label of a synthetic prescription, an intent of a specific note, etc. The manual input module 114 may utilize feedback to update specific weights, labels, etc. of the ML model(s). In addition, the feedback received by the manual input module 114 may be used to update or improve other components of the prescription standardization system 100 accordingly. It is noted that the data augmentation module 112 may continue to improve or update the ML model(s) and/or prescription standardization system 100 on a periodic or continuous basis. As such, (5) may occur simultaneously or concurrently with (4) and/or with other elements outlined in FIG. 4.

FIG. 5 illustrates an example routine 500 for inferring a standardized medication prescription from a medication prescription. The routine 500 may be executed by the standardization engine 104 and various components of the prescription standardization system 100. Specifically, routine 500 may be executed by a processor, not shown, of user device 102.

At block 502, the standardization engine 104 may receive a request for a standardized medication prescription for a prescription. In some embodiments, the standardization engine 104 receives the request for the standardized medication prescription from a user device, such as the user device 102. For example, standardization engine 104 may receive a request from a user of an external system, such as a pharmacy, hospital, or even patient-facing system. The request may come from a pharmacist, a pharmacy technician, a patient, a medical provider, and the like. In some embodiments, the standardization engine 104 may receive the request from the user device 102 over the network 120.

At block 504, the standardization engine 104 may obtain a raw medication prescription 202 corresponding to the prescription. The raw medication prescription 202 may, in some examples, include prescription data, medication data, and/or patient data associated with the prescription. The raw medication prescription may correspond to the request for the standardized medication prescription. For example, the request for the standardized medication prescription may include the medication prescription 202. Alternatively, or in addition, the medication prescription 202 corresponding to the request may be accessed and/or obtained by the standardization engine 104 from a different source, such as a server, database, etc. For example, the medication prescription 202 may transmitted from the prescriber network to the standardization engine 104. In some embodiments, the prescription standardization system 100 receives the medication prescription 202 from a remote device, server, or other source, transmitted over the network 120.

In some embodiments, the medication prescription 202 may include or correspond to a prescription (e.g., written, typed) that may identify patient data (e.g., name, address), prescriber information, drug or controlled substance name, dosage form, drug strength, quantity, directions for use, intake frequency, refill options, date, and the like. In some embodiments, the medication prescription 202 may be "raw" and may comprise text written by the prescriber or medical provider. In addition, the medication prescription 202 may contain information in addition to the prescription, such as prescription notes, patient history information, prescriber information, and the like. For example, patient history information may indicate a quantity and frequency of a particular drug previously prescribed. Prescription notes may include any insurance information, alternative or substitute drugs, and/or any miscellaneous information related to the prescription.

At block 506, the standardization engine 104 (and/or the normalization module 108) may normalize the raw medication prescription 202 into a normalized raw medication prescription. In some embodiments, the standardization engine 104 omits normalization of the medication prescription 202 if the medication prescription 202 has already been normalized by an external process or system. To normalize the medication prescription 202, the normalization module 108 may standardize or normalize the terminology of the medication prescription 202. As noted herein, the medication prescription 202 may contain text-based directions from the prescriber. As such, the medication prescription 202 may contain errors, acronyms, incomplete information, alternative drug names, common pharmacological jargon, inconsistencies, and the like. In normalizing the medication prescription 202, the normalization module 108 may fact-check the medication prescription 202 against the domain knowledge data store 116. Normalization may also correct past prescription processing errors and provide clear instructions to the patient. This may prevent prescription abuse and potential safety hazards to the patient. In some embodiments, the normalization module 108 may access the domain knowledge data store 116 in order to determine or obtain standardized terminology. For example, the normalization module 108 may replace outdated terminology (e.g., drug names, abbreviations) with current terminology.

In addition, to normalize the medication prescription 202, the normalization module 108 may verify or authenticate the medication prescription 202 according to domain knowledge. Authenticating the medication prescription 202 includes verifying the medication prescription 202 against the domain knowledge data store 116. For example, the normalization module 108 may identify, highlight, or flag errors in the medication prescription 202. The normalization module 108 may identify an anomaly in the quantity of a drug prescribed (e.g., a quantity far exceeding historical prescriptions), an inconsistency in the directions for use (e.g., prescribing a topical medication to be ingested), incorrect drug name.

At block 508, the standardization engine 104 (and/or the inferring module 110) may input the normalized raw medication prescription into a machine learning model. The inferring module 110 may input the normalized medication prescription into a single ML model configured to infer the standardized medication prescription 204, which may include several pieces of inferred information from the medication prescription 202. In some embodiments, the inferring module 110 inputs the normalized medication prescription into multiple ML models configured to inter the standardized medication prescription 204.

At block 510, the standardization engine 104 (and/or the inferring module 110) may parse, with the ML model, the normalized raw medication prescription into atomic medical information. For example, to parse the normalized medication prescription, the ML model may divide, separate, or apportion the medication prescription 202 into atomic medical information. In some embodiments, the inferring module 110 utilizes any AI-based or ML model, such as the ML model(s) stored in the ML model store 118 to parse the medication prescription 202. Alternatively, or in addition, the inferring module 110 may utilize any algorithm, process, or method other than machine learning to parse the medication prescription 202. In some examples, the inferring module 110 may output atomic medical information based on the medication prescription 202.

At block 512, the standardization engine 104 (and/or the inferring module 110) may infer, with the machine learning model, a standardized medication prescription 204 from the atomic medical information. Based on the medication prescription 202 input to the ML model, the ML model may generate and output a standardized medication prescription 204. The standardized medication prescription 204 may comprise a number of fields, each relating to an aspect of the medication prescription 202. Each field may be related to information crucial for a pharmacist, technician, or patient to understand the prescription. For example, fields may include a minimal quantity per dose, a maximum quantity per dose, a daily administration minimum frequency, a daily administration maximum frequency, a cadence, hours of administration, or an average daily administration frequency. As such, the inferring module 110 may infer each field from the atomic medical information of a medication prescription 202.

In addition, the standardization engine 104 may augment the standardized medication prescription with domain knowledge data. The domain knowledge data, as described herein, may comprise historical pharmacy directions.

At block 514, the standardization engine 104 may transmit the standardized medication prescription 204. For example, the standardization engine 104 may transmit the standardized medication prescription 204 to a user device, such as the user device 102. The standardization engine 104 may transmit the standardized medication prescription 204 to a pharmacy to be accessed by a pharmacist or technician. In addition, the standardized medication prescription 204 may be transmitted to a pharmacy to be printed with the corresponding filled prescription. In some examples, the standardized medication prescription 204 is transmitted directly to a user or patient.

Routine 500 may include additional elements, not pictured, that may be implemented by the standardization engine 104 and various components of the prescription standardization system 100. Specifically, in some embodiments, routine 500 is be executed by a processor, not shown, of user device 102. The processor of the user device 102 may, in addition to the blocks 502-514 of routine 500, train the ML model on a set of training samples, the training samples comprising synthetic prescriptions.

In addition, in some embodiments, the processor of the user device 102 may, in addition to the blocks 502-514 of routine 500, augment the standardized medication prescription 204 with domain knowledge data. For example, in some embodiments, the inferring module 110 may augment, enrich, supplement, or revise the output of the ML model with information from the knowledge database 208. For example, the medication prescription 202 may include the direction "take 1 tablet by mouth every day in the morning." Although the standardization engine 104 may normalize and parse the medication prescription 202, the medication prescription 202 does not specify an hour of administration (HOA). For example, "in the morning" may refer to different hours in the morning (e.g., 8 a.m., 10 a.m.). In this example, the inferring module 110 may supplement the standardized medication prescription 204 with the medication's standard administration and/or patient history.

In addition, in some cases, the processor of the user device 102 may, in addition to blocks 502-514 of routine 500, calculate a dosage calculation based on the atomic medical information. For example, the inferring module 110 may calculate an average daily administration frequency based on information provided in the medication prescription 202.

Figure 6:
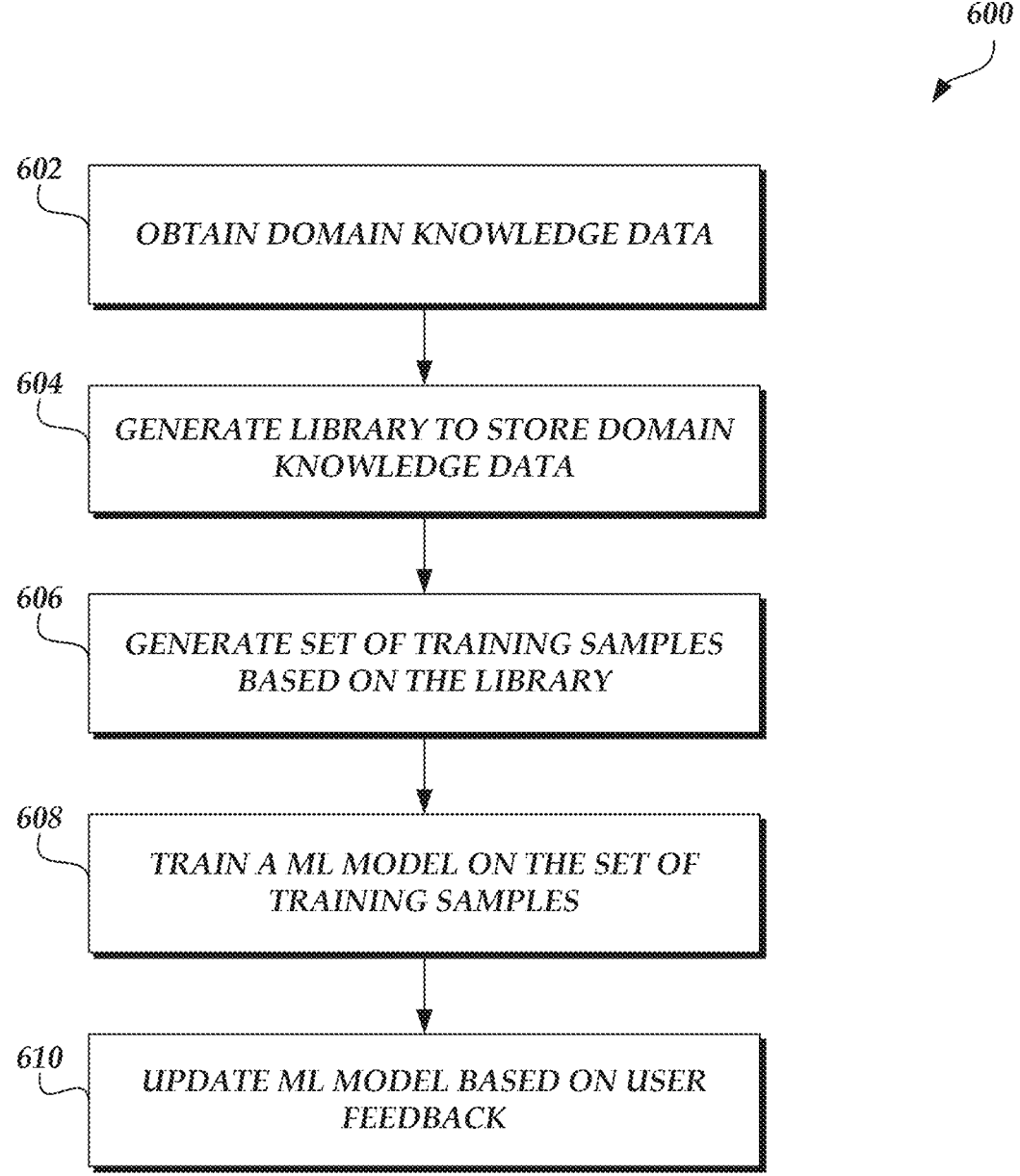
FIG. 6 illustrates an example routine for generating training set data to train a machine learning model of a prescription standardization system.

FIG. 6 illustrates an example routine 600 for generating training set data to train a machine learning model of a prescription standardization system. In some embodiments, the routine 600 is executed by the active learning engine 106 and various components of the prescription standardization system 100. Specifically, routine 600 may be executed by a processor, not shown, of user device 102. At block 602, domain knowledge data may be obtained. For example, the data augmentation module 112 of the active learning engine 106 may obtain the domain knowledge data from the domain knowledge data store 116.

The domain knowledge data comprises logic to infer a standardized medication prescription 204 from a medication prescription 202. For example, domain knowledge data store 116 may hold domain knowledge data relating to medicine, pharmacy, and related fields. For example, domain knowledge data may include historical pharmacy direction data (e.g., past prescriptions), drug information, drug interaction information, drug dosage information, active ingredients information, inactive ingredients information, drug names (e.g., generic name, brand name), and the like. The domain knowledge data store 116 includes historical pharmacy prescription data 212. Historical pharmacy prescription data 212 may include any information related to past prescriptions, directions, notes by medical providers or pharmacists, and the like.

At block 604, the data augmentation module 112 may generate a library to store the domain knowledge data. Each library may comprise any data management or organization system maintained by the data augmentation module 112 to organize the domain knowledge data. For example, the data augmentation module 112 may generate a library with subfolders and/or subsections to organize domain knowledge data specific to historic prescriptions of a certain drug (e.g., organized by date, patient, dosage level). In some embodiments, the libraries may be stored locally within the active learning engine 106, or may be stored remotely and accessible via a server or network. In some embodiments, the data augmentation module 112 may update the library, e.g., on a periodic basis.

At block 606, the data augmentation module 112 may generate a set of training samples based on the library. In some embodiments, each training sample of the set of training samples comprises a synthetic prescription. For example, training samples may include synthetic or synthetic prescriptions that mimic realistic prescriptions. In some embodiments, the data augmentation module 112 may utilize the contents of the libraries, such as domain knowledge corresponding to a particular drug and/or historic prescription data, to generate synthetic prescriptions. In addition, the data augmentation module 112 may utilize any rule-based or generative artificial intelligence (AI) approach to generate the training samples. The data augmentation module 112 may generate synthetic prescriptions of varying difficulty levels. For example, the data augmentation module 112 may generate simple synthetic prescriptions intended to be an "easy" case (e.g., a prescription with all the inferred information explicitly included). The data augmentation module 112 may also generate complex prescriptions with missing information, incorrect or inconsistent information, and/or other difficult variations of real scenarios. For example, a synthetic prescription may contain a complex intake direction, such as "twice a day every day three days at 8 a.m. and 6 p.m., excluding weekends" or the like. In some examples, the data augmentation module 112 may generate a synthetic prescription based on a subset of information from the libraries. Synthetic prescriptions and/or other training data may be tailored, such as to provide targeted training for the ML model(s). For example, synthetic prescriptions focused on training the ML model(s) to infer complex dosage calculations may be generated by the data augmentation module 112. In this example, the data augmentation module 112 may retrieve or access libraries pertaining to historic prescriptions containing complex dosage directions in order to generate similar synthetic prescriptions.

In addition, at block 606, the data augmentation module 112 may label each synthetic prescription with the appropriate "correct" inferred information. For example, the data augmentation module 112 may generate a synthetic prescription that reads: "take 1 to 2 tablets by mouth daily." In this example, the data augmentation module 112 may label each portion of the synthetic prescription with the correct inferred output. The following labels may be applied to each portion of the synthetic prescription: minimal quantity per dose="1"; maximal quantity per dose="2"; daily administration minimal frequency="[once] daily"; daily administration maximal frequency="[once] daily"; cadence="daily"; hours of administration=N/A; average daily administration frequency="1." In some embodiments, more or less labels may be given to the synthetic prescription.

The synthetic prescriptions and/or other training data sets may be stored in the libraries maintained by the data augmentation module 112 or elsewhere and accessible via servers or networks, such as network 120.

At block 608, the active learning engine 106 (and/or the data augmentation module 112) may train a ML model on the set of training samples. The ML model may be trained to infer the standardized medication prescription 204 from the medication prescription 202. For example, the ML model(s) may be trained on a specific set of synthetic prescriptions generated by the data augmentation module 112. The active learning engine 106 and/or data augmentation module 112 may conduct training on the ML model(s) in order to train the ML model(s) to infer a specific set of information from a medication prescription. In addition, the active learning engine 106 and/or data augmentation module 112 may conduct training to train the ML model(s) to infer all requested information from a medication prescription.

At block 610, the active learning engine 106 may update the ML model with user feedback. The user feedback may correspond to pharmacist logic or knowledge typically used to infer the standardized medication prescription 204. To update the ML models, the active learning engine 106 may first receive user input, such as via the manual input module 114. The manual input module 114 may receive user input related to any aspect of the prescription standardization system 100. For example, the user input may relate to a correction in a synthetic prescription, a corrected label of a synthetic prescription, an intent of a specific note, etc.

In response to receiving the user feedback, the active learning engine 106 may tune and/or improve aspects of the ML model(s), active learning engine 106, and ultimately any aspect of the prescription standardization system 100. To improve aspects of the system, the manual input module 114 may update specific weights, labels, etc. of the ML model(s). In addition, the user feedback received by the manual input module 114 may be used to update or improve other components of the prescription standardization system 100 accordingly. For example, the information stored in the domain knowledge data store 116 may be updated. It is noted that the data augmentation module 112 may continue to improve or update the ML model(s) and/or prescription standardization system 100 on a periodic or continuous basis. As such, 610 may occur simultaneously or concurrently with 608 and/or with other blocks in routine 600. Those skilled in the art will recognize that routine 600 may include fewer or more (not pictured) elements to be implemented by the active learning engine 106 and/or various components of the prescription standardization system 100. In some embodiments, routine 600 may be executed by a processor, not shown, of user device 102. Moreover, the processor of the user device 102 may, in addition to the blocks 602-610 of routine 600, input a medication prescription 202 to the ML model, parse, with the ML model, the medication prescription into atomic medical information, and infer, with the ML model, a standardized medication prescription 204 from the atomic medical information.

The processor of the user device 102 may, in addition to the blocks 602-610 of routine 600, augment the standardized medication prescription 204 with domain knowledge data. For example, in some embodiments, the inferring module 110 may augment, enrich, supplement, or revise the output of the ML model with information from the knowledge database 208. For example, the medication prescription 202 may include the direction "take 1 tablet by mouth every day in the morning." Although the standardization engine 104 may normalize and parse the medication prescription 202, the medication prescription 202 does not specify an hour of administration (HOA). For example, "in the morning" may refer to different hours in the morning (e.g., 8 a.m., 10 a.m.). In this example, the inferring module 110 may supplement the standardized medication prescription 204 with the medication's standard administration and/or patient history.

The processor of the user device 102 may, in addition to the blocks 602-610 of routine 600, calculate a dosage calculation based on the atomic medical information. For example, the inferring module 110 may calculate an average daily administration frequency based on information provided in the medication prescription 202. In this regard, the medication prescription 202 may contain the following text directed to administration of a prescribed medication: "three times daily (every 8 hours), three days weekly on Monday, Wednesday, and Friday." The inferring module 110 may infer, from this medication prescription 202, that the average daily administration frequency is 9/7, to account for the three times daily over three days weekly.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system is a cloud-based computing system whose processing resources are shared by multiple distinct business entities or other users.

FIG. 7 is a block diagram that illustrates the general architecture of a computing system implementing the prescription standardization system 100 of FIG. 1. The general architecture of the system depicted in FIG. 7 includes an arrangement of computer hardware and software that may be used to implement aspects of the present disclosure. The hardware may be implemented on physical electronic devices, as discussed in greater detail below. The system may include many more (or fewer) elements than those shown in FIG. 7. It is not necessary, however, that all of these generally conventional elements be shown in order to provide an enabling disclosure. Additionally, the general architecture illustrated in FIG. 7 may be used to implement one or more of the other components illustrated in FIG. 1. As illustrated, the system includes a processing unit 702, a network interface 704, a computer-readable medium drive 706, and an input/output device interface 708, all of which may communicate with one another by way of a communication bus.

The network interface 704 may provide connectivity to one or more networks or computing systems. The processing unit 702 may thus receive information and instructions from other computing systems or services via the network. The processing unit 702 may also communicate to and from memory 710 and further provide output information for an optional display (not shown) via the input/output device interface 708. The input/output device interface 708 may also accept input from an optional input device (not shown).

The memory 710 may contain computer program instructions (grouped as units in some embodiments) that the processing unit 702 executes in order to implement one or more aspects of the present disclosure, along with data used to facilitate or support such execution. While shown in FIG. 7 as a single set of memory 710, memory 710 may in practice be divided into tiers, such as primary memory and secondary memory, which tiers may include (but are not limited to) random access memory (RAM), 3D XPOINT memory, flash memory, magnetic storage, and the like. For example, primary memory may be assumed for the purposes of description to represent a main working memory of the system, with a higher speed but lower total capacity than a secondary memory, tertiary memory, etc.

The memory 710 may store an operating system 712 that provides computer program instructions for use by the processing unit 702 in the general administration and operation of the prescription standardization system 100. The memory 710 may further include computer program instructions and other information for implementing aspects of the present disclosure. For example, in one embodiment, the memory 710 includes a standardization engine 104 and an active learning engine 106.

The standardization engine 104 may represent code executable to generate a standardized medication prescription from a raw medication prescription, e.g., from the ML model stored in the ML model store 118. The standardization engine 104 may apply the raw medication prescription into the ML model to be parsed into atomic medical information, from which the ML model may generate a standardized medication prescription. The active learning engine 106 may represent code executable to provide data augmentation to the components of the standardization engine 104, such as the normalization module 108 and the inferring module 110.

The system of FIG. 7 is one illustrative configuration of such a device, of which others are possible. For example, while shown as a single device, a system may in some embodiments be implemented as a logical device hosted by multiple physical host devices. In other embodiments, the system may be implemented as one or more virtual devices executing on a physical computing device. While described in FIG. 7 as a prescription standardization system 100, similar components may be utilized in some embodiments to implement other devices shown in the prescription standardization system 100 of FIG. 7.

Some or all of the statistical analysis methods described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

The processes described herein or illustrated in the figures of the present disclosure may begin in response to an event, such as on a predetermined or dynamically determined schedule, on demand when initiated by a user or system administrator, or in response to some other event. When such processes are initiated, a set of executable program instructions stored on one or more non-transitory computer-readable media (e.g., hard drive, flash memory, removable media, etc.) may be loaded into memory (e.g., RAM) of a server or other computing device. The executable instructions may then be executed by a hardware-based computer processor of the computing device. In some embodiments, such processes or portions thereof may be implemented on multiple computing devices and/or multiple processors, serially or in parallel.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm elements described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like.

A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

Unless otherwise explicitly stated, articles such as "a" or "an" should generally be interpreted to include one or more described items throughout this application. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C. Unless otherwise explicitly stated, the terms "set" and "collection" should generally be interpreted to include one or more described items throughout this application. Accordingly, phrases such as "a set of devices configured to" or "a collection of devices configured to" are intended to include one or more recited devices. Such one or more recited devices can also be collectively configured to carry out the stated recitations. For example, "a set of servers configured to carry out recitations A, B and C" can include a first server configured to carry out recitation A working in conjunction with a second server configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A system comprising:
   a memory to store specific computer-executable instructions; and
   a processor in communication with the memory, wherein the processor is to execute the specific computer-executable instructions to at least:
   receive, from a user device, a request for a standardized medication prescription;
   obtain a raw medication prescription, wherein the raw medication prescription includes medication data, medication direction data, and patient data associated with the prescription;
   normalize the raw medication prescription into a normalized raw medication prescription;
   input the normalized raw prescription direction to a machine learning model;
   parse, with the machine learning model, the normalized raw medication prescription into atomic medical information;
   infer, with the machine learning model, a standardized medication prescription from the atomic medical information;
   supplement, with the machine learning model, the standardized medication prescription, wherein supplementing comprises:
   identifying a portion of the standardized medication prescription;
   generating supplemental information related to the portion of the standardized medication prescription based on a knowledge database; and
   revising the standardized medical prescription to include the supplemental information; and
   transmit the supplemented standardized medication prescription to the user device.

2. The system of claim 1, wherein the processor is to execute further specific computer-executable instructions to at least train the machine learning model on a set of training samples, the set of training samples comprising synthetic prescriptions.

3. The system of claim 1, wherein the processor is to execute further specific computer-executable instructions to at least augment the standardized medication prescription with domain knowledge data.

4. The system of claim 3, wherein the domain knowledge data comprises historical pharmacy directions.

5. The system of claim 1, wherein to infer, the processor is to execute further specific computer-executable instructions to calculate a dosage calculation based on the atomic medical information.

6. The system of claim 1, wherein the standardized medication prescription includes at least one of a minimal quantity per dose, a maximum quantity per dose, a daily administration minimum frequency, a daily administration maximum frequency, a cadence, hours of administration, or an average daily administration frequency.

7. The system of claim 1, wherein to normalize the raw medication prescription, the processor is to execute further specific computer-executable instructions to at least:

normalize text of the raw medication prescription according to domain knowledge data; and authenticate the raw medication prescription according to the domain knowledge.

8. A computer-implemented method comprising:

obtaining a medication prescription, wherein the medication prescription includes medication data, medication direction data, and patient data associated with the prescription;

inputting the medication prescription to a machine learning model;

parsing, with the machine learning model, the medication prescription into atomic medical information;

inferring, with the machine learning model, a standardized medication prescription from the atomic medical information;

supplementing, with the machine learning model, the standardized medication prescription, wherein supplementing comprises:

identifying a portion of the standardized medication prescription;

generating supplemental information related to the portion of the standardized medication prescription based on a knowledge database; and revising the standardized medical prescription to include the supplemental information; and transmitting the supplemented standardized medication prescription to the user device.

9. The computer-implemented method of claim 8, further comprising training the machine learning model on a set of training samples, the set of training samples comprising synthetic prescriptions.

10. The computer-implemented method of claim 8, further comprising augmenting the standardized medication prescription with domain knowledge data.

11. The computer-implemented method of claim 10, wherein the domain knowledge data comprises historical pharmacy directions.

12. The computer-implemented method of claim 8, wherein inferring the standardized medication prescription further comprises calculating a dosage calculation based on the atomic medical information.

13. The computer-implemented method of claim 8, wherein the standardized medication prescription includes, at least one of a minimal quantity per dose, a maximum quantity per dose, a daily administration minimum frequency, a daily administration maximum frequency, a cadence, hours of administration, or an average daily administration frequency.

14. The computer-implemented method of claim 8, further comprising:

normalizing text of the medication prescription according to domain knowledge data; and authenticating the medication prescription according to the domain knowledge data.

* * * * *